United States Patent
Berestov

(10) Patent No.: US 6,317,481 B1
(45) Date of Patent: Nov. 13, 2001

(54) STEREO X-RAY IMAGE PROCESSING

(75) Inventor: Alexander Berestov, San Jose, CA (US)

(73) Assignee: Canon Kabushiki Kaisha, Tokyo (JP)

(*) Notice: Subject to any disclaimer, the term of this patent is extended or adjusted under 35 U.S.C. 154(b) by 0 days.

(21) Appl. No.: 09/428,867

(22) Filed: Oct. 27, 1999

(51) Int. Cl.$^7$ .................................................. A61B 6/02
(52) U.S. Cl. .............................................. 378/41; 378/42
(58) Field of Search ......................................... 378/41, 42

(56) References Cited

U.S. PATENT DOCUMENTS

| | | | |
|---|---|---|---|
| 4,214,267 | * | 7/1980 | Roese et al. ............................ 378/42 |
| 4,737,972 | * | 4/1988 | Schoolman ............................. 378/41 |
| 5,090,038 | * | 2/1992 | Asahina ................................. 378/41 |
| 5,163,076 | * | 11/1992 | Koyama ................................. 378/42 |
| 5,233,639 | * | 8/1993 | Marks .................................... 378/42 |
| 5,852,646 | * | 12/1998 | Klotz et al. ............................. 378/8 |

OTHER PUBLICATIONS

Talukdar, A. et al.; Modeling and Optimization of Rotational C–Arm Stereoscopic X–Ray Angiography, IEEE Transactions on Medical Imaging, vol. 18, No. 7, pp. 604–616, (Jul. 1999).

Woods, A. et al.; Image Distortions in Stereoscopic Video System, SPIE, vol. 1915 Stereoscopic Displays and Applications IV, pp. 36–48, (1993).

\* cited by examiner

*Primary Examiner*—Robert H. Kim
*Assistant Examiner*—Allen C. Ho
(74) *Attorney, Agent, or Firm*—Fitzpatrick, Cella, Harper & Scinto

(57) ABSTRACT

A system, method, and computer-readable medium for capturing radiographic images and processing the captured images into stereo images. The images are captured using an X-ray imaging system that rotates freely about an anchor point and captures images of the patient or other object from different angles. The images are transmitted to a graphics engine (130) that rotates and adjusts points in the images in order to place them in the same plane and may also combines the two images into a single stereo image. Additional error processing methods are provided in order to reduce resulting distortion.

18 Claims, 4 Drawing Sheets

(2 of 4 Drawing Sheet(s) Filed in Color)

STEREO X-RAY IMAGE PROCESSING

RELATED APPLICATIONS

The subject matter of this application is related to he subject matter of the commonly owned application Ser. No. 09/112, 704, titled "Coloration And Display Of Data Matrices" filed on Jul. 8, 1998 by Alexander Berestov, and application Ser. No. 09/428, 286, titled "Fast Epipolar Line Adjustment of Stereo Pairs", filed concurrently, also by Alexander Berestov, the contents of which are incorporated by reference as if fully disclosed herein.

FIELD OF THE INVENTION

The present invention relates to the field of diagnostic imaging procedures. More specifically, the invention relates to the field of digital manipulation of X-ray images to create stereo images.

BACKGROUND

X-ray technology has been applied to a wide range of medical, industrial, and scientific problems. In part, this is a consequence of the varied properties of X rays, including differential absorption, quantitative measurement of absorption, diffraction by crystals, fluorescence of characteristic radiation, and biological effects produced by X rays. One of the earliest applications of X-ray technology was to medicine, being used in both diagnosis and therapy. Diagnostics include the detection of bone fractures, foreign objects in the body, dental cavities, and diseased conditions such as cancer. In therapeutic treatment, X rays are used to stop the spread of malignant tumors, and in conjunction with other non-invasive procedures. X-ray technology has also been used in a number of industrial applications. For example, X-ray radiographs have been used to detect flaws in castings that are inaccessible to direct observation and to measure the thickness of materials.

The study of X rays has also played a vital role in theoretical physics, especially in the development of quantum mechanics. As a research tool, X rays enabled physicists to confirm experimentally the theories of crystallography. By using X-ray diffraction methods, crystalline substances may be identified and their structure determined. Virtually all present-day knowledge in this field was either discovered or verified by X-ray analysis. X-ray diffraction methods can also be applied to powdered substances that are not crystalline but that display some regularity of molecular structure. By means of such methods, chemical compounds can be identified and the size of ultramicroscopic particles can be established. Chemical elements and their isotopes may be identified by X-ray spectroscopy, which determines the wavelengths of their characteristic line spectra. Several elements were discovered by analysis of X-ray spectra.

A number of recent applications of X rays in research are assuming increasing importance. Microradiography, for instance, produces fine-grain images that can be enlarged considerably. Color radiography is also used to enhance the detail of X-ray photographs; in this process, differences in the absorption of X rays by a specimen are shown as different colors. Extremely detailed and analytical information is provided by the electron microprobe, which uses a sharply defined beam of electrons to generate X rays in an area of specimen as small as 1 micrometer (about $1/25,000$ in) square. One limitation on the usefulness of X-ray technology, however, has been the limited ability to provide three-dimensional information of the object being examined. It is difficult to create a stereo image of the structure inside an object from two-dimensional radiographs.

Several complicated systems have been devised to obtain three dimensional information, including transmission X-ray microscopes. X-ray microscopy combines X-ray transmission systems with tomographical reconstruction methods, enabling recreation of three-dimensional information of the internal microstructure. These methods and resulting images can be used to analyze the two- and three-dimensional anatomical structure using a set of flat cross-sectional images. These methods rely on the contrast in the images, which represents a mixed combination of density and compositional information. In some cases, the compositional information can be further separated from the density information. This method, however, requires a large number of different cross-sectional images of an object resulting in increased exposure to potentially harmful radiation. Additionally, the images must be taken with great care in order to provide the correct cross-sections.

Another X-ray imaging device is a Computerized Axial Tomography scanner (also known as a "CAT scanner," or "CT scanner"), which is a medical diagnostic test device that combines the use of X rays with computer technology. A series of X-ray beams from many different angles are used to create cross-sectional images of the patient's body. These images are assembled in a computer into a three-dimensional picture (in the way similar to tomographical reconstructure) that can display organs, bones, and tissues in great detail.

However, these facilities are complicated, expensive and are often not accessible to most researchers and users. What is needed, then, is a system and method for extracting three dimensional information from two-dimensional X-ray images that is relatively simply to use, accessible to both small and large medical and research facilities, while providing limited exposure of a patient or other object to radiation.

DISCLOSURE INVENTION

The present invention comprises a system and method for converting radiograph pairs into stereo images. The system comprises an X-ray tube (110) for emitting X rays, a screen or film (120) for capturing two or more images and a graphics engine (130) for adjusting and combining the captured images. The system further comprises a rod (140), or similar support mechanism, for suspending the tube (110) and screen (120) while enabling free rotation of the tube (110) and screen (120) about a point between the tube and screen.

The present invention further includes a method for converting radiograph pairs, wherein each radiograph is captured from a distinct location in space, into a stereo image. The radiographs may be taken using the X-ray system of the present invention, or a similarly capable X-ray imaging device may be used. The radiographs are transmitted to a graphics engine (130) for processing. The engine 130 may be directly attached to the X-ray imaging system for quicker processing, or may be transmitted using any number of digital transmission means. The transmitted radiographs are rotated (320) by the graphics engine (130) to place them in the same, or parallel, planes. Each of the points in the image are recalculated (330) accordingly. The engine (130) also removes keystone distortion by locating matching points in the images and correcting the image accordingly. The images are combined and optionally colored to further enhance the stereo effect.

BRIEF DESCRIPTION OF THE DRAWINGS

The file of this patent contains at least one drawing executed in color. Copies of this patent with color drawings will be provided by The Patent and Trademark Office upon request and payment of necessary fees.

DETAILED DESCRIPTION OF THE PREFERRED EMBODIMENTS

An X Ray is a type of penetrating electromagnetic radiation, having a shorter wavelength than light, and produced by bombarding a target, usually made of tungsten, with high-speed electrons. The first X-ray tube was the Crookes tube, a partially evacuated glass bulb containing two electrodes, named after its designer, the British chemist and physicist Sir William Crookes. When an electric current passes through such a tube, the residual gas is ionized and positive ions, striking the cathode, eject electrons from it. These electrons, in the form of a beam of cathode rays, bombard the glass walls of the tube and produce X rays.

Most of the X-ray tubes in present-day use are modified Coolidge tubes. The Coolidge tube is highly evacuated and contains a heated filament and a target. It is essentially a thermionic vacuum tube in which the cathode emits electrons because the cathode is heated by an auxiliary current and not because it is struck by ions as in the earlier types of tubes. The electrons emitted from the heated cathode are accelerated by the application of a high voltage across the tube. As the voltage is increased, the minimum wavelength of the radiation decreases.

The larger and more powerful tubes have water-cooled anticathodes to prevent melting under the impact of the electron bombardment. The widely used shock proof tube is a modification of the Coolidge tube with improved insulation of the envelope (by oil) and grounded power cables. Devices, such as the betatron, are used to produce extremely hard X rays, of shorter wavelength than the gamma rays emitted by naturally radioactive elements. The X-ray tube 110 of the present invention comprises one or more of the tubes described above that produce and emit X rays, including the Crookes Tube, Coolidge Tube, modified Coolidge Tube, and betatron.

Figure 1:
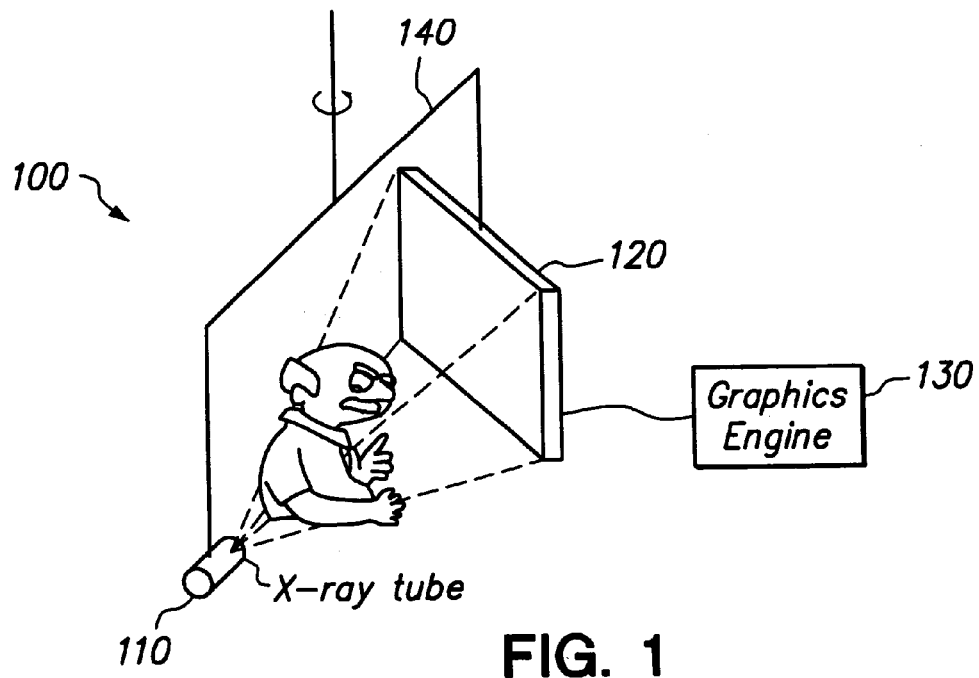
FIG. 1 illustrates the X-ray imaging system of the present invention.

Referring now to FIG. 1, a system for capturing three-dimensional X-ray images is shown. The X-ray stereo imaging system comprises an X-ray tube 110, a screen 120, and a graphics engine 130, said tube 110 and screen 120 rotating synchronously about a patient (or another object) and transmitting X-ray images to the graphics engine 130. The tube 110 produces and emits X rays that pass through the patient (or other object) to create varying impressions on the screen 120. The screen 120 comprises a regular X-ray film, a digital sensor plate, or any other medium that may be used to capture the X-ray image. The captured image is either transmitted directly to the graphics engine 130, if the digital plate is used, or converted into a digital format.

The screen 120, or photographic plate, captures the X rays and provides an image of the object. X rays affect a photographic emulsion in the same way light does. Absorption of X-ray radiation by any substance depends upon its density and atomic weight. The lower the atomic weight of the material, the more transparent it is to X rays of given wavelengths. When the human body is x-rayed, the bones, which are composed of elements of higher atomic weight than the surrounding flesh, absorb the radiation more effectively and therefore cast darker shadows on a photographic plate. The screen 120 of the present invention comprises a digital plate but may also comprise standard X-ray film that uses a chemical emulsion or coating that is capable of visually depicting absorbed X rays.

Once the screen 120 and tube 110 have been placed in the correct alignment, a series of pictures are taken of the patient at different angles by rotating the screen 120 and tube 110 system about the patient. Alternatively, the patient may be rotated rather than the screen, but in most medical applications it is preferable to keep a patient still to avoid injury. The X-ray imaging system 100 takes regular radiographic pictures as it is rotated about the patient.

The graphics engine 130 comprises a hardware unit with at least one processor, such as a personal computer, capable of performing the method of the present invention. The method is described in detail with reference to FIG. 3 below. If the X-ray images are captured using a digital screen, then X-ray images may be transmitted directly to the graphics engine 130. If the radiograph images are not captured digitally, an additional digital capture device, such as a computer scanner, may be used to place the analog or film based images into a digital format.

Once the images are in a digital format they are transmitted to the graphics engine 130 by any means of digital transmission. Digital transmission means includes, but is not limited to, transmitting files over computer networks, such as sending the image to a server or node over a local area network; a direct link between the image capture device and the engine, such as a direct link cable or similar wire line; storage and retrieval from a digital recording medium, such as floppy or compact disk. Other means for transmitting information to the engine are also available as is known to those skilled in the art.

Figure 2:
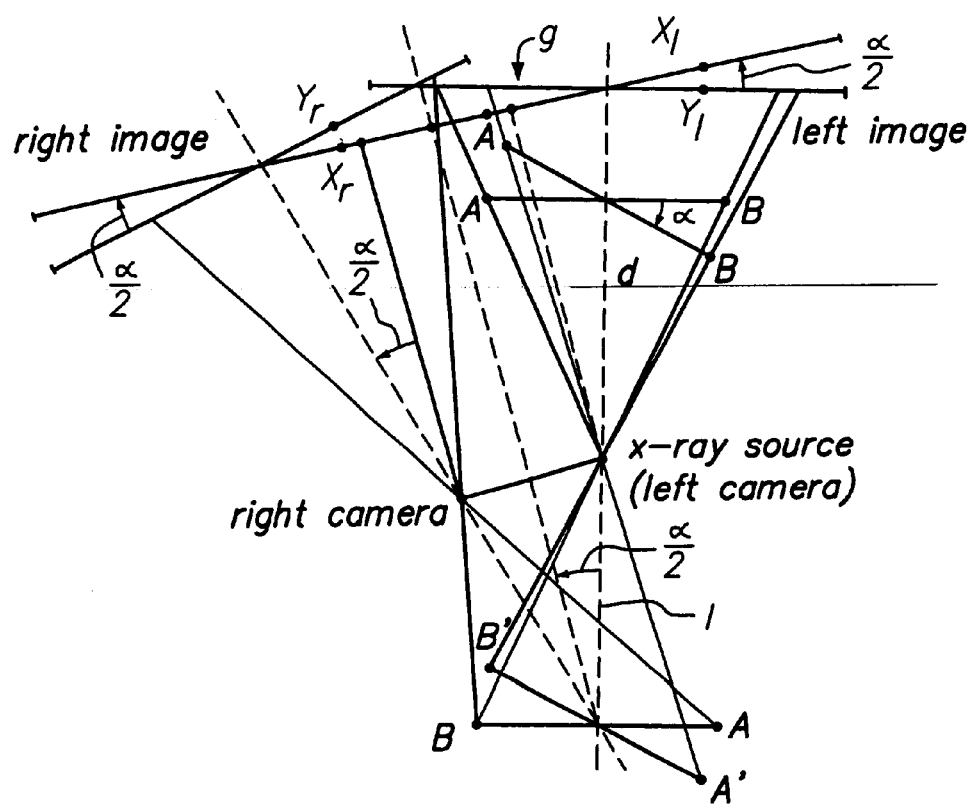
FIG. 2 illustrates the geometry of the imaging system.

FIG. 2 shows the optical geometry of the system and will be used to illustrate the method of the present invention. The object marked by letters A and B is located at the distance 1 from the X-ray source. The screen 120, which has the width g, is placed at the distance d from X-ray tube 110 behind the patient (or object).

The X rays are emitted from the tube 110 almost from one point, meaning this system has a geometry nearly identical to the optical geometry of a pinhole camera. The X-ray source is analogous to the pinhole of the camera and d is the equivalent of the focal length of the camera.

As an initial matter, the system is used to take a first image of the object. The images are taken according to standard protocol and procedures implemented when taking radiographs. The system is then rotated α and a second image is taken. Although the second image is necessary for generating the final stereo image, as further described with reference to FIG. 5 below, more than many images may be taken of the object and used to assemble a stereo movie.

In the present system, the convergence point, the point where the optical axes of the "cameras" intersect, is at the center of the object. The position of the convergence point, along with our a priori knowledge of the lengths and distances associated with the images, can be used to combine the images into a single stereo image.

Figure 3:
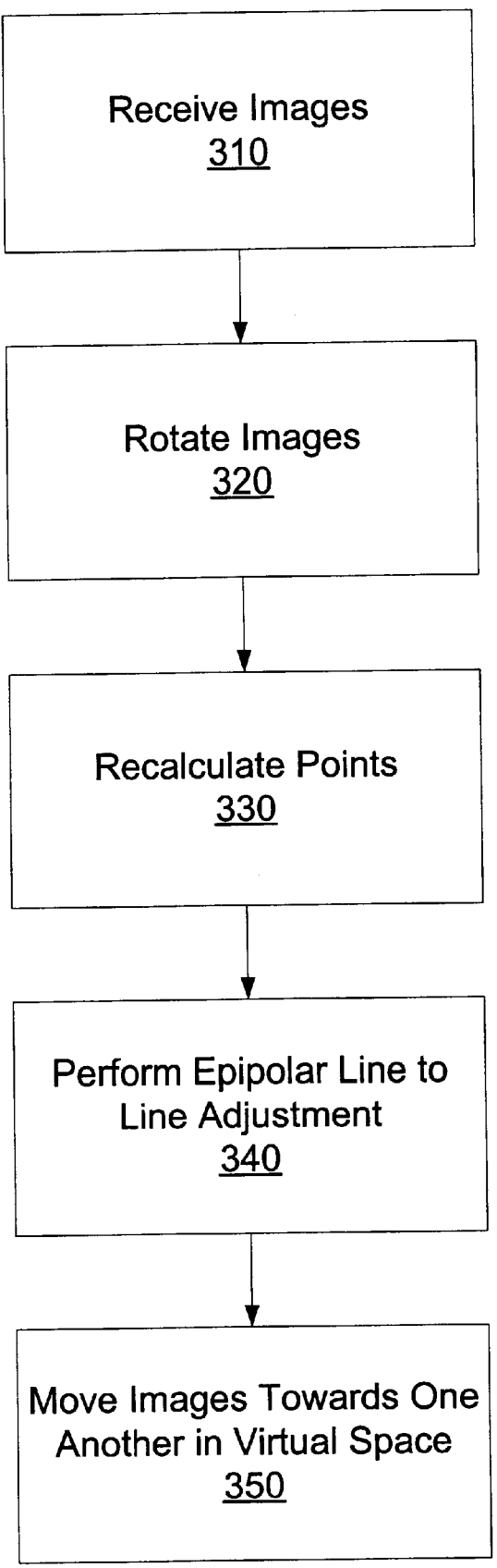
FIG. 3 is a flowchart of a preferred method for making stereo images using radiographs generated using the X-ray imaging system.
Figure 4:
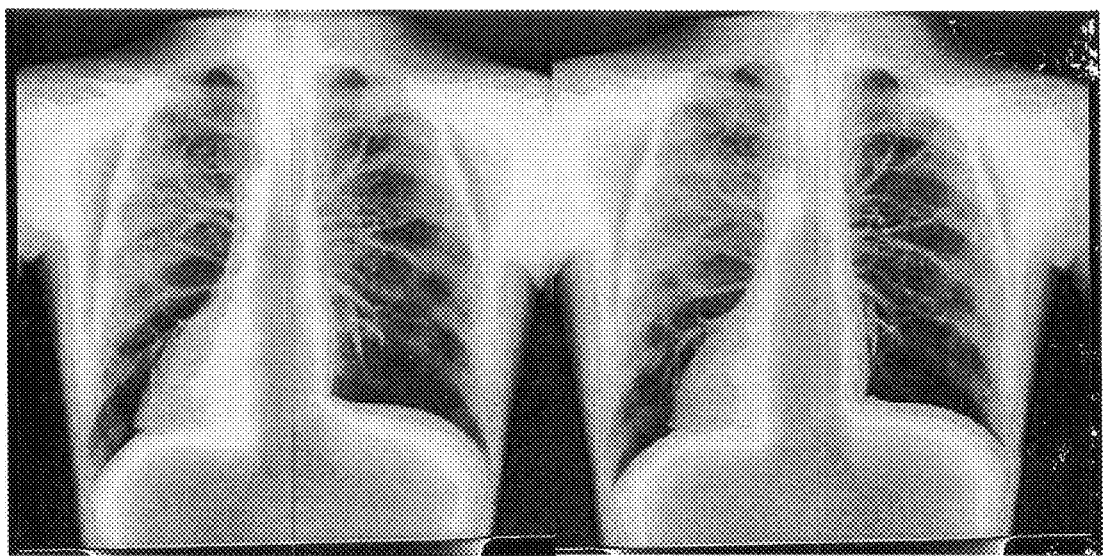
FIG. 4 is a first and second color image generated using the system of the present invention.

Referring now to FIG. 3, a method for creating a stereo image using radiographs, preferably generated by operating the X-ray system of the present invention, is shown. This method will be described as being performed by the graphic engine 130, but other processing engines capable of performing the method of the present invention may also be used.

The graphics engine 130 receives 310 two or more digital images taken of the subject from two different locations. When the graphics engine 130 begins combining the images taken by the imaging system 100, the toed-in configuration of the cameras has some disadvantages. One disadvantage is the depth plane curvature, which could lead to incorrectly perceived relative object distances. This distortion can be eliminated by making the two images parallel. In order to make them parallel, the machine rotates 320 the images in order to place the images in the same plane. More specifically, the machine rotates the first image clockwise for $\alpha/2$ and rotates the second image for $\alpha/2$ counter-clockwise. This transformation places the images in the same plane, which is parallel to the base line between two locations used to capture the images.

During this transformation, the points in the images are recalculated 330 by the engine 130. Each of the points in the images must be recalculated to a point along the new plane. The coordinate x of the point in the old image, which goes into $y^{th}$ pixel in the rotated image, is calculated using the following equation:

$$x_{r,l} = \frac{w}{2} \pm \frac{dw}{g} \frac{y_{r,l} \cos \frac{\alpha}{2}}{\frac{dw}{g} \pm y_{r,l} \sin \frac{\alpha}{2}},$$

where w is the width of the image in pixels and $\alpha$ is the angle of rotation between the location where the first and second images were captured using the X-ray imaging system 100 of the present invention. If an alternative X-ray imaging system is used, $\alpha$ is defined as the angle of rotation between the location of the first and second image placed on an imaginary circle about the object of interest, wherein the imaginary circle has a radius equal to the distance between the X-ray tube and the object, said circle further centered about the object.

Another error associated with combining these images is keystone distortion. Keystone distortion causes vertical parallax in the stereoscopic image and is caused by the fact that the camera sensor captures the images at two imaging locations that are located in different planes. To eliminate this error, the machine performs 340 epipolar line to line adjustment on the images. Application of this method also eliminates errors that appear because the axis of the object rotation is not perfectly vertical. This method is further described in U.S. patent application Ser. No. 09/428,286 filed on Oct. 27, 1999, entitled "Fast epipolar line-to-line adjustment of stereo pairs," which patent application is commonly assigned with the present application and is hereby incorporated by reference in its entirety into the present patent application.

In order to complete the method, the graphics engine 130 moves 350 the images towards one another in virtual space. More specifically, the engine 130 moves 350 the images toward each other for $$Mh = \frac{dw}{g} \sin \frac{\alpha}{2}$$

pixels to put the optical axis of the "camera" in the middle of the stereo image, where M is the frame magnification, which is the ratio of display area width to camera sensor width.

This method differs from Computerized Axial Tomography, which involves taking cross-sectional images of the patient's body and often further involves moving the patient back and forth. Thus, the present invention reduces exposure time and standard radiology equipment can be used to assemble the system. Use of a digital plate can make the procedure even faster, further decreasing the exposure time. More importantly, the method can be used to correct the distortion effects that hampered previous efforts to use standard radiology equipment for sophisticated image capture and three-dimensional processing.

Figure 5:
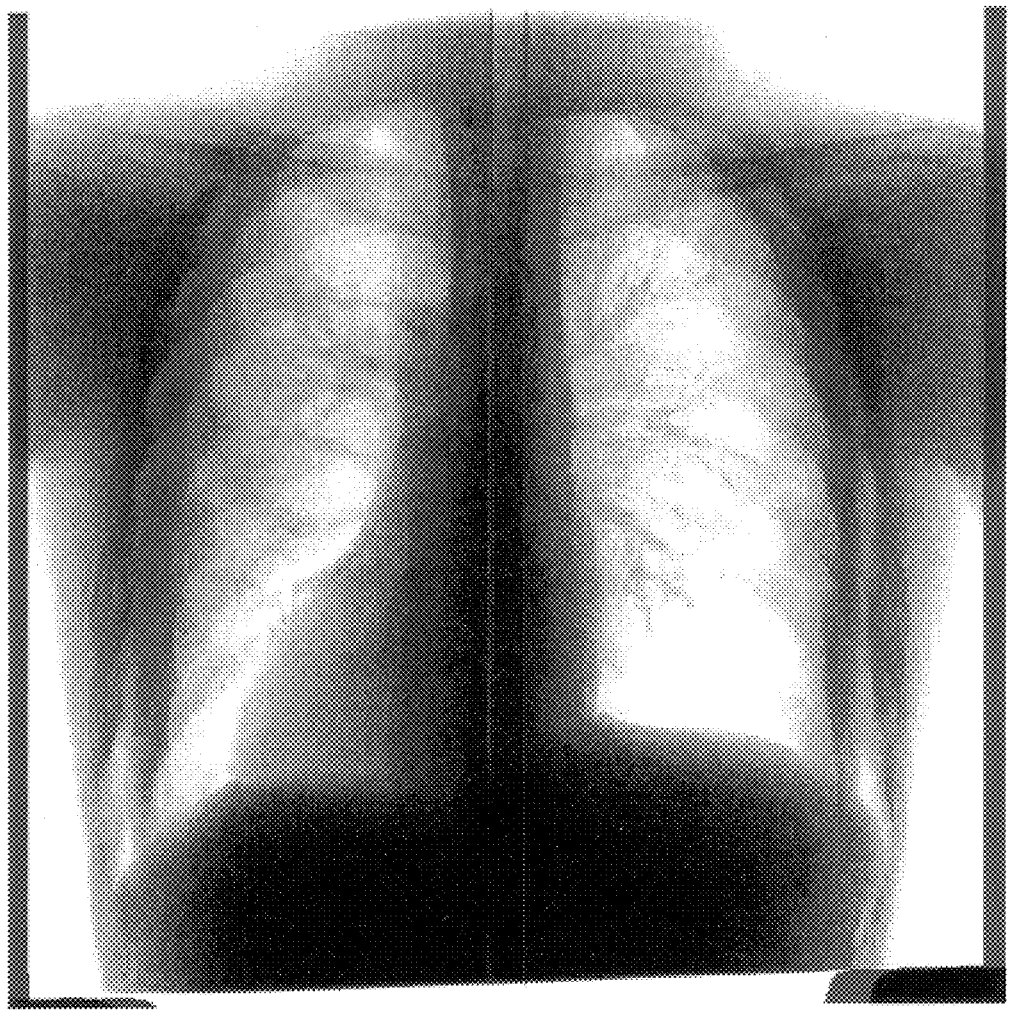
FIG. 5 is a color stereo image generated by combining a first and second image using the system and method of the present invention.

FIG. 5 shows an anaglyph picture created using the described method. Red and blue glasses are helpful in viewing the stereo effect. A further extension of this method enables creation of a stereo movie. In order to create a stereo movie, the X-ray imaging system takes pictures every degrees until a full rotation is completed. The method for creating a stereo image, described above, is then applied to each image and its clockwise neighbor. These stereo pairs may then be placed in a frame sequence in a "movie" format.

Since the optical geometry of the system is known a priori, it is possible to modify the processing of the images in any way the viewer desires. For example, a viewer may wish to increase or decrease stereo effect. This can be accomplished by combining different image pairs, such as pairing images one and three rather than one and two and two and three. The images can also be colored using the method described in the patent application Ser. No. 09/112,704, titled "Coloration and Display of Data Matrices." FIG. 5 shows the result of the application of this coloring method to the stereo images.

While the present system and method have been described with reference to specific embodiments, those skilled in the art will recognize that these procedures may be applied to all kinds of digital and analog images. Furthermore, the processing engine, X-ray screen and X-ray tube may comprise any number of different devices. Thus, the scope of this invention and claims should not be limited by the described implementations.

What is claimed is:

1. An imaging system comprising:
   a support mechanism, having a first end and second end;
   coupled to the first end of said support mechanism, an X-ray tube adapted by emitting X rays;
   coupled to the second end of said support mechanism, a screen for capturing the emitted X rays;
   coupled to the support mechanism, at least one anchor for supporting the support mechanism and attached tube and screen, wherein said anchor(s) allow(s) full rotational movement of the support mechanism about the anchor; and
   coupled to the screen, a graphics engine for rotating and adjusting the captured images into a single stereo image.

2. The system of claim 1, wherein the graphics engine is a processor in a personal computer.

3. The system of claim 1, wherein the X-ray tube is a Crookes Tube.

4. The system of claim 1, wherein the X-ray tube is a Coolidge Tube.

5. The system of claim 1, wherein the X-ray tube is a modified Coolidge Tube.

6. The system of claim 1, wherein the X-ray tube is a Betatron.

7. The system of claim 1, wherein the screen is digital X-ray capture plate.

8. The system of claim 1, wherein the screen comprises X-ray film, said system further comprising an image conversion device for converting an image on the X-ray film into a digital image.

9. The system of claim 8, wherein the image conversion device is a computer scanner.

10. A method for creating a stereo radiograph image, said method comprising:

receiving a first and second digital representation of a first and second radiograph, respectively, of an object, wherein said first radiograph is taken by fixing the distance, D, between an object and an X-ray tube and said second radiograph is taken by rotating said X-ray tube around said object α degrees while maintaining distance D;

rotating images captured on the radiographs at the respective midpoints of the radiographs, such that the images are aligned with a line connecting the midpoints of the first image and the second image;

calculating a shift amount, wherein the shift amount is the amount the images must be shifted towards each other to align the centers of the images;

moving the pixels of the first and second image towards each other by the calculated shift amount;

combining the pixels of the first image and the second image into a composite image.

11. The method of claim 10, further comprising the steps of:

removing any red color from the pixels being combined from the first image prior to combining the pixels; and removing any blue color from the pixels being combined from the second image prior to combining the pixels.

12. The method of claim 10, wherein the step of rotating the images comprises the step of calculating a new location for each pixel in the image using the equation $$x_{r,l} = \frac{w}{2} \pm \frac{dw}{g} \frac{y_{r,l} \cos \frac{\alpha}{2}}{\frac{dw}{q} \pm y_{r,l} \sin \frac{\alpha}{2}},$$

where w is the width of the image in pixels and α is the angle of rotation between the location where the first image was captured and the location where the second image was captured.

13. The method of claim 10, wherein the step of calculating the shift amount is performed using the equation $$Mh = \frac{dw}{g} \sin \frac{\alpha}{2}$$

where M is the frame magnification.

14. A method for making a digital radiograph movie, the method comprising the following steps:

capturing radiographic images using an X-ray imaging system, wherein the system is rotated a degrees between each consecutive image;

processing the radiographic images by applying the method of claim 11 to the images, wherein the images being provided to the processing engine for processing are separated by an intervening image; and displaying each of the processed images such that there are brief time lapses between the display of one processed image and the next processed image.

15. A system for capturing radiographic images, said system comprising:

a support mechanism, having a first end and second end;

coupled to the first end of said support mechanism, means for emitting X rays;

coupled to the second end of said support mechanism, means for capturing the wavelengths of the X rays;

coupled to the support mechanism, means for supporting the support mechanism, wherein said means for supporting the mechanism allows full rotational movement of the support mechanism about the supporting means; and coupled to means for processing the captured images according to the method of claim 11.

16. A computer-readable medium containing a computer program for aligning two images, said program containing instructions for directing the computer to execute the steps of:

receiving a first and a second digital representation of a first and second radiograph, respectively, of an object, wherein said first radiograph is taken by fixing the distance, D, between an object and an X-ray tube and said second radiograph is taken by rotating said X-ray tube around said object a degrees while maintaining distance D;

rotating images captured on the radiographs at the respective midpoints of the radiographs, such that the images are aligned with a line connecting the midpoints of the first and second image;

calculating a shift amount, wherein the shift amount is the amount each image must be shifted towards the other image to align the centers of the images;

moving the pixels of each of the first and second image towards one another by the calculated shift amount; and combining the pixels and the first and second image into a composite image.

17. The computer-readable medium of claim 16, further comprising instructions for directing the computer to execute the steps of:

removing any red color from the pixels being combined from the first image prior to combining the pixels; and removing any blue color from the pixels being combined from the second image prior to combining the pixels.

18. The computer-readable medium of claim 16, wherein the instructions for directing the computer to execute the step of rotating the images further comprise instructions for calculating a new location for each pixel in the image using the equation $$x_{r,l} = \frac{w}{2} \pm \frac{dw}{g} \frac{y_{r,l} \cos \frac{\alpha}{2}}{\frac{dw}{q} \pm y_{r,l} \sin \frac{\alpha}{2}},$$

where w is the width of the images in pixels, d is the focal length of the camera, and α is the angle of rotation between the location where the first image and the location where the second image was captured.

* * * * *

UNITED STATES PATENT AND TRADEMARK OFFICE
CERTIFICATE OF CORRECTION

PATENT NO. : 6,317,481 B1  
DATED : November 13, 2001  
INVENTOR(S) : Alexander Berestov Page 1 of 1

It is certified that error appears in the above-identified patent and that said Letters Patent is hereby corrected as shown below:

Column 1,
Line 4, "he" should read -- the --.

Column 2,
Line 39, "DISCLOSURE INVENTION" should read -- DISCLOSURE OF INVENTION --.

Column 6,
Line 23, "every" should read -- every $\alpha$ --;
Line 51, "X rays;" should read -- X-rays; --; and
Line 53, "X rays;" should read -- X-rays; --.

Column 8,
Line 29, "a" should read -- $\alpha$ --.

Signed and Sealed this

Twenty-third Day of April, 2002

*Attest:*

JAMES E. ROGAN  
*Attesting Officer*  *Director of the United States Patent and Trademark Office*